United States Patent [19]

Wojtkowski

[11] Patent Number: 4,599,451

[45] Date of Patent: Jul. 8, 1986

[54] PROCESS FOR PREPARING ORTHO-(ALKYLTHIO)PHENOLS

[75] Inventor: Paul W. Wojtkowski, Wilmington, Del.

[73] Assignee: E. I. DuPont de Nemours and Company, Wilmington, Del.

[21] Appl. No.: 740,030

[22] Filed: May 31, 1985

[51] Int. Cl.$^4$ .................................................. C07C 149/36
[52] U.S. Cl. .................................... 568/54; 568/45; 568/46; 568/47; 568/49; 568/50; 568/52
[58] Field of Search .................. 568/47, 46, 50, 49, 568/52, 54, 69, 45

[56] References Cited

U.S. PATENT DOCUMENTS

| | | | |
|---|---|---|---|
| 2,923,743 | 2/1960 | Delfs et al. | 568/54 |
| 3,134,818 | 5/1964 | Farah et al. | 568/52 |
| 3,697,601 | 10/1972 | Fujisawa et al. | 568/46 |
| 4,324,920 | 4/1982 | McKinnie et al. | 568/54 |

*Primary Examiner*—Donald G. Daus
*Assistant Examiner*—Mary E. Ceperley

[57] ABSTRACT

The process of the invention involves reacting a phenol with a dialkyl disulfide in the presence of a zirconium phenoxide catalyst to prepare the corresponding ortho-(alkylthio)phenol.

21 Claims, No Drawings

PROCESS FOR PREPARING ORTHO-(ALKYLTHIO)PHENOLS

BACKGROUND OF THE INVENTION

This invention relates to a process for preparing ortho-(alkylthio)phenols by reacting certain phenols with dialkyl disulfides in the presence of zirconium phenoxide catalysts.

The compounds resulting from the process of the invention are useful as intermediates for the preparation of certain sulfonylurea herbicides.

U.S. Pat. No. 4,324,920 discloses a process for the preparation of ortho-(alkylthio)phenols by contacting phenols with dialkyl disulfides in the presence of catalytic amounts of aluminum phenoxide.

U.S. Pat. No. 2,923,743 discloses a process for the preparation of aryl-alkyl thioethers from aromatic compounds (such as xylene, phenol, 4-chlorophenol) and dialkyl disulfides, in the presence of a catalyst such as aluminum chloride, ferric chloride or bleaching earth (e.g., Tonsil ®).

None of the above disclosures involve the process of the present invention. None of the above disclosures involve the catalyst of the invention.

SUMMARY OF THE INVENTION

A process has been discovered whereby ortho-(alkylthio)phenols can be prepared by reaction of a phenol with a dialkyl disulfide in the presence of a zirconium phenoxide catalyst. The process of the invention may be also described as follows:

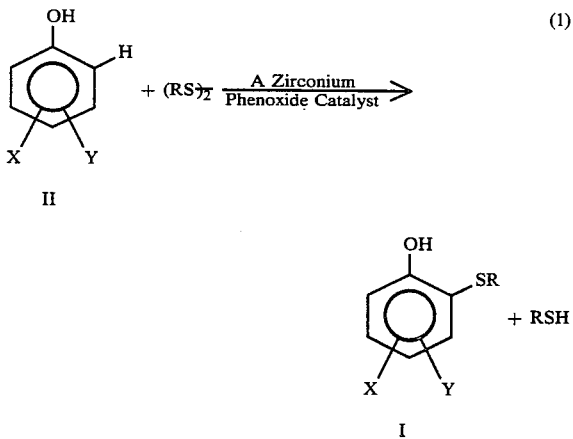

In the phenols of Formulas I and II above, X and Y are independently H, OH, $C_1$–$C_6$ alkyl, $OR_1$, $SR_1$, Cl, F, I, Br or aryl substituted with $C_1$–$C_6$ alkyl, $OR_1$, $SR_1$, Cl, F, I or Br; when X and Y are on adjacent carbon atoms, they may be taken together to form $CH=CH-CH=CH$; R is $C_1$–$C_6$ alkyl; and $R_1$ is $C_1$–$C_6$ alkyl with the proviso that:

(a) X and Y cannot simultaneously be OH; and (b) when R is $C_4$–$C_6$ alkyl, the carbon bonded to the heteroatom must be substituted by one or two hydrogen atoms.

The reaction is generally carried out by combining excess phenol (molar basis) with the disulfide and 0.01 to 0.5 molar equivalents (relative to disulfide) of the catalyst. The reaction is heated, with or without a solvent, at 100°–300° C. and atmospheric pressure with continuous removal of mercaptan by-product. Upon completion, the (alkylthio)phenol produced is isolated by standard procedures. The process of the invention may be carried out under the conditions shown below:

|  | General | Preferred | Most Preferred |
|---|---|---|---|
| Molar ratio of phenol to disulfide | 5:1 to 1:3 | 5:1 to 1:3 | 5:1 to 1:1 |
| Molar ratio of catalyst to disulfide | 0.99 to 0.01 | 0.5 to 0.01 | 0.2 to 0.05 |
| Temperature | 90–300° C. | 110–210° C. | 110–180° C. |
| Substrate | Generic scope of Equation 1 | X = H, Cl, $C_1$–$C_3$ alkyl, Y = H R = $C_1$–$C_3$ alkyl | X = H, Cl, $CH_3$ Y = H R = $C_1$–$C_2$ alkyl |
| Catalyst | A zirconium phenoxide catalyst | A zirconium phenoxide prepared from zirconium tetrachloride or a zirconium tetraalkoxide. | A zirconium phenoxide prepared in situ from zirconium tetrachloride and the phenol. |

The preferred process of the invention is conducted with a phenol of Formula II wherein X is H or 4-Cl; Y is H and R is $CH_3$ or $C_2H_5$.

What is meant by a zirconium phenoxide catalyst is a tetravalent zirconium species substituted by 1–4 phenoxy or substituted phenoxy groups.

DETAILED DESCRIPTION OF THE INVENTION

This invention describes a novel process for the preparation of ortho-(alkylthio)phenols which consists of contacting phenols having at least one ortho hydrogen atom with a dialkyl disulfide in the presence of a catalytic amount of a zirconium phenoxide. The molar ratio of catalyst to disulfide is less than 1, preferably between 0.01 and 0.5 and most preferably 0.05 to 0.2. The process is conducted at temperatures from about 100°–300° C. with preferred temperatures being 110°–210° C. The reaction produces as a by-product alkyl mercaptan corresponding to the dialkyl disulfide used. The reaction is performed in such fashion to continuously remove or allow escape of this alkyl mercaptan.

The zirconium catalysts can be prepared in a variety of ways either in a separate reaction or in situ. For example, if the phenol to be used is phenol itself, pure zirconium tetraphenoxide catalyst can be prepared and isolated prior to its use as catalyst. It can be prepared by reacting zirconium n-propoxide with phenol in p-cymene solvent at elevated temperatures, and then removing volatiles including n-propanol by distillation. Purification of the remaining solid by filtration, dissolution, precipitation, washing, and drying gives pure zirconium tetraphenoxide which can then be added to a mixture of phenol and dialkyl disulfide. Suitable zirconium phenoxide catalysts can also be prepared in situ. For example, excess phenol can be reacted with zirconium tetrachloride at elevated temperatures of about 100° to 200° C., for an extended time period, for example 2-24 hours, with removal of hydrogen chloride by-product by purging with an inert gas such as nitrogen. Dialkyl disulfide can then be added directly and the reaction allowed to proceed. Another in situ method entails mixing excess phenol and zirconium tetrachloride in a solvent such as toluene or xylene followed by slow removal of the toluene or xylene by distillation. This aids in removal of HCl, and generally results in shorter catalyst preparation time (a total of ~2 hours) than the previous method. Still another method for forming a suitable catalyst in situ is by reacting the phenol with a zirconium alkoxide, and then removing the alcohol corresponding to the alkoxide by, for example, distillation. If distillation is used, the alcohol corresponding to the alkoxide should have a boiling point below that of the phenol used. For example, in the case of phenol, zirconium n-propoxide could be used and n-propanol readily removed by distillation. Other methods of preparing zirconium phenoxides not specified here may be used also.

The preferred in situ method of catalyst preparation from the above described methods is to react zirconium tetrachloride with the phenol to be used in the reaction in xylene or toluene solvent.

Dialkyl disulfide, RSSR, which may be employed in the practice of this invention has R from $C_1-C_6$ with the proviso that if R is $C_4-C_6$ alkyl, the carbon bonded to the heteroatom must be substituted by one or two hydrogen atoms. The preferred disulfides are dimethyl disulfide, diethyl disulfide, and di-n-propyl disulfide and the most preferred disulfides are dimethyl disulfide and diethyl disulfide.

The phenols used herein can be mono- or polynuclear, such as naphthols, and can contain more than one hydroxyl such as dihydroxybenzenes. The aryl portion of the phenol may be linked to or fused with other cyclic systems, including heterocyclic systems such as those containing cyclo oxygen, nitrogen, or sulfur rings. Substituents besides hydroxyl can be present on the phenol as long as they do not interfere with the reaction. For example, the phenols may be substituted with $C_1-C_6$ alkyl, alkoxy, alkylthio, Cl, Br, F, I, and aryl where the aryl can be substituted with $C_1-C_6$ alkyl, alkoxy, alkylthio, Cl, Br, F and I. The preferred phenols are phenol, 4-chlorophenol, and 4-methylphenol.

In practicing the process of this invention, the catalyst is preferably prepared in situ and the dialkyl disulfide added to the phenol-catalyst mixture. The reaction is then allowed to proceed for a time and temperature which can vary depending upon such considerations as the boiling point of the dialkyl disulfide, the melting point of the phenol, etc. In a preferred aspect, the mixture is maintained at or near its reflux temperature, and the reaction is allowed to proceed for the period of time which results in the maximum yield of the desired product. The mercaptan by-product corresponding to the disulfide used is removed continuously, for example, by purging with an inert gas, or by distillation, or otherwise. The reaction is preferably performed at atmospheric pressure, but pressures above or below atmospheric may be used also.

The final product can be obtained and purified from the reaction mixture by conventional methods such as distillation. Although some para and disubstituted phenols are formed also, they can be readily separated from the desired product by distillation.

The reaction can be conducted with a wide range of molar ratios of the phenol to disulfide, generally about 5:1 to 1:3, and an excess of the phenol is preferred. The reaction is generally performed without solvent, but solvent can be used provided it does not interfere with the reaction. An excess of the phenol can also serve as solvent. The reaction is normally performed under an inert atmosphere, and anhydrous conditions are desirable but not necessary provided that moisture levels are not high enough to interfere with the reaction.

The following examples serve to illustrate the invention.

EXAMPLE 1

Preparation of Zirconium Phenoxide

Phenol (50 g), zirconium n-propoxide (10 g), and p-cymene (100 ml) were combined. The mixture was distilled through a 10 cm Vigreux column until all volatile components were removed. The cooled product was taken up in a mixture of methylene chloride (100 ml) and toluene (200 ml). This was filtered, and then concentrated under reduced pressure to a volume of ca. 50 ml. The concentrate was filtered to give 6.3 g of solid which was washed with petroleum ether, and dried under high vacuum for one hour to give white solid product.

Calcd. for $Zr(OC_6H_5)_4$: C, 62.19; H, 4.32; Found: C, 61.92; H, 4.42.

EXAMPLE 2

Preparation of Ortho-(Ethylthio)phenol

Zirconium phenoxide (4.0 g, 0.0086 moles) was added to phenol (8.9 g, 0.095 moles) and ethyl disulfide (10.5 g, 0.086 moles). The mixture was heated under nitrogen for 6.5 hours during which the temperature slowly increased to 195° C. Ethyl mercaptan was removed continuously by distillation. The mixture was distilled at 0.4 mm mercury to a maximum head temperature of 102° C. yielding 12.2 g of distillate. Gas chromatographic (GC) analysis indicated the distillate contained 5.0 g of ortho-(ethylthio)phenol (38% yield).

EXAMPLE 3

Preparation of Ortho-(Ethylthio)phenol

Zirconium tetrachloride (23.4 g, 0.1 mole) was added to phenol (141.2 g, 1.5 moles). The mixture was slowly heated to 156° C. under nitrogen and maintained at this temperature overnight while allowing HCl to escape. The mixture was cooled to ca. 100° C. and ethyl disulfide (122.3 g, 1 mole) was added. The mixture was heated under nitrogen while ethyl mercaptan was removed continuously by distillation. Heating was continued for a total of 7 hours during which temperature slowly increased to 198° C. Distillation of the mixture at 0.4 mm mercury to a maximum head temperature of 101° C. yielded 134.7 g of distillate. GC analysis indicated the distillate contained 53.4 g of phenol (38% recovered) and 63.7 g of ortho-(ethylthio)phenol (41% yield). Fractional distillation through a 5 inch Vigreux column yielded, after removal of phenol, a main fraction of 99.2% pure ortho-(ethylthio)phenol distilling at 125°–127° C. at 30 mm mercury.

EXAMPLE 4

Preparation of Ortho-(Ethylthio)phenol

A mixture of phenol (87.5 g, 0.93 moles), xylene (100 ml), and zirconium tetrachloride (6.0 g, 0.026 moles) was heated to reflux under a slow nitrogen stream. The xylene was distilled through a 10 inch Vigreux column. The distillation was continued over a 2 hour period until the reaction mixture reached 177° C. Approximately 10 g of phenol was distilled with the xylene. The reaction mass was cooled to 150° C., and ethyl disulfide (62.0 g, 0.50 moles) was added. The reaction mixture was heated to 152° C., then heated slowly over a 5 hour period to 180° C., and finally held at 180° C. for an additional 10 hours. Ethyl mercaptan was removed continuously by distillation. The reaction mixture was cooled to 100° C., then vacuum distilled at 100 mm mercury until the pot temperature reached 200° C. to give 70.8 g of distillate. GC analysis indicated the distillate contained 34.0 g of ortho-(ethylthio)phenol (44% yield).

A similar run using phenol (142 g, 1.51 moles), toluene (150 ml), zirconium tetrachloride (6.0 g, 0.026 moles), and ethyl disulfide (62.0 g, 0.50 moles) gave ortho-(ethylthio)phenol (36.0 g, 46% yield).

EXAMPLE 5

Preparation of Ortho-(Ethylthio)phenol

To phenol (35.3 g, 0.37 moles) was added 10.6 g of zirconium n-propoxide in n-propanol consisting of 21.6% zirconium (0.025 mole) and 10.8% free n-propanol. The mixture was distilled at atmospheric pressure removing n-propanol. Ethyl disulfide (30.6 g, 0.25 moles) was added, and the mixture was heated under nitrogen while ethyl mercaptan was removed continuously by distillation. Heating was continued for a total of 6.5 hours during which temperature slowly increased to 200° C. Distillation of the mixture at 0.5 mm mercury to a maximum head temperature of 84° C. yielded 31.7 g of distillate. GC analysis indicated the distillate contained 12.4 g of phenol (35% recovered) and 15.9 g of ortho-(ethylthio)phenol (41% yield).

EXAMPLE 6

Preparation of Ortho-(Methylthio)phenol

Zirconium tetrachloride (23.4 g, 0.1 mole) was added to phenol (141.2 g, 1.5 moles). The mixture was slowly heated to 150° C. under nitrogen and maintained at this temperature for 12 hours during which HCl was allowed to escape. The mixture was cooled to ca. 100° C. and methyl disulfide (94.2 g, 1 mole) was added. The mixture was heated under nitrogen for 15 hours during which temperature was increased slowly to 159° C. Methyl mercaptan was allowed to escape continuously. Distillation of the mixture at 1.4 mm mercury to a maximum head temperature of 113° C. yielded 125.6 g of distillate. GC analysis indicated the distillate contained 59.1 g of phenol (42% recovered) and 54.2 g of ortho-(methylthio)phenol (39% yield). The unreacted phenol was removed from the distillate by fractional distillation through a 12 cm glass helices packed column. The remaining material was fractionally distilled through a 5 inch Vigreux column yielding a main fraction of 99.6% pure ortho-(methylthio)phenol distillating at 112°–114° C. at 30 mm mercury.

EXAMPLE 7

Preparation of Ortho-(n-Propylthio)phenol

Zirconium tetrachloride (23.4 g, 0.1 mole) was added to phenol (141.2 g, 1.5 moles). The mixture was slowly heated to 157° C. under nitrogen and maintained at this temperature overnight while allowing HCl to escape. The mixture was cooled to ca. 100° C., and n-propyl disulfide (150.3 g, 1 mole) was added. The mixture was heated under nitrogen while n-propyl mercaptan was removed continuously by distillation. Heating was continued for a total of 8 hours during which temperature slowly increased to 203° C. Distillation of the mixture at 0.5 mm mercury to a maximum head temperature of 115° C. yielded 138.1 g of distillate. GC analysis indicated the distillate contained 49.3 g phenol (35% recovered) and 67.2 g of ortho-(n-propylthio)phenol (40% yield). Fractional distillation through a 5 inch Vigreux column yielded, after removal of phenol, a main fraction of 99.4% pure ortho-(n-propylthio)phenol distilling at 135° C. at 30 mm mercury.

EXAMPLE 8

Preparation of 2-Ethylthio-4-t-Butylphenol

To 4-t-Butylphenol (10.0 g, 0.067 moles) was added 2.8 g zirconium n-propoxide in n-propanol consisting of 21.6% zirconium (0.007 mole) and 10.8% free propanol. The mixture was distilled at atmospheric pressure removing 1.8 g of n-propanol. To the mixture was added ethyl disulfide (8.2 g, 0.067 moles). The mixture was heated under nitrogen while ethyl mercaptan was removed continuously by distillation. Heating under nitrogen was continued for a total of 142 hours during which temperature slowly increased to 194° C. The mixture was cooled, hydrolyzed by addition of water, and made acid with concentrated HCl. The mixture was extracted with ether. The ether extracts were dried over magnesium sulfate, filtered, and concentrated on a rotary flash evaporator. GC analysis of the concentrate indicated only two major components, 2.5 g of 4-t-butylphenol and 6.8 g of 2-ethylthio-4-t-butylphenol (49% yield).

EXAMPLE 9

Preparation of 2-Methylthio-4-Chlorophenol

A mixture of 4-chlorophenol (15.0 g, 0.12 moles) and cyclohexane (8 ml) was distilled to remove cyclohexane and water. To the dry p-chlorophenol was added 3.3 g of zirconium n-propoxide in n-propanol consisting of 21.6% zirconium (0.008 mole) and 10.8% free propanol. The mixture was distilled at atmospheric pressure under nitrogen removing 1.0 g of n-propanol. To the resultant mixture was added methyl disulfide (7.1 g, 0.075 moles). The mixture was heated under nitrogen at reflux for 43 hours during which the temperature increased to 180° C. The mixture was cooled, hydrolyzed by addition of water, treated with concentrated HCl to dissolve solids, and extracted with ether. The ether extracts were dried over magnesium sulfate, filtered, and concentrated on a rotary flash evaporator. GC analysis of the concentrate indicated only two major components, 5.9 g of 4-chlorophenol and 8.1 g of 2-methylthio-4-chlorophenol (62% yield).

What is claimed is:

1. A process for the preparation of ortho-(alkylthio)-phenols comprising reacting a phenol of the formula:

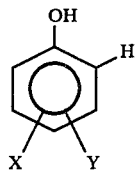

wherein
X and Y are independently H, OH, $C_1$–$C_6$ alkyl, $OR_1$, $SR_1$, Cl, F, I, Br or aryl substituted with $C_1$–$C_6$ alkyl, $OR_1$, $SR_1$, Cl, F, I or Br, or when X and Y are on adjacent carbon atoms, they may be taken together to form CH=CH—CH=CH; and
$R_1$ is $C_1$–$C_6$ alkyl; provided that X and Y cannot simultaneously be OH;
with a dialkyl disulfide of the formula, $(RS)_2$
wherein R is $C_1$–$C_6$ alkyl;
provided that when R is $C_4$–$C_6$ alkyl, the carbon bonded to the heteroatom must be substituted by one or two hydrogen atoms;
at a temperature of 100°–300° C. and at atmospheric pressure in the presence of a zirconium phenoxide catalyst with the continual removal of mercaptan by-product, said phenol and disulfide being in a molar ratio of 3:1–1:3 of phenol to disulfide and the catalyst and disulfide being in a molar ratio of 0.99:1–0.01:1 of catalyst to disulfide.

2. The process of claim 1 wherein the molar ratio of phenol to sulfide is 1:1–5:1 and the molar ratio of zirconium catalyst to disulfide is 0.50:1–0.01:1.

3. The process of claim 1 wherein a solvent is used.

4. The process of claim 1 wherein no solvent is used.

5. The process of claim 2 wherein a solvent is used.

6. The process of claim 2 wherein no solvent is used.

7. The process of claim 1 wherein the temperature is 110°–210° C.

8. The process of claim 1 wherein the temperature is 110°–180° C.

9. The process of claim 2 wherein the temperature is 110°–210° C.

10. The process of claim 2 wherein the temperature is 110°–180° C.

11. The process of claim 1 wherein X is H, Cl or $C_1$–$C_3$ alkyl; Y is H and R is $C_1$–$C_3$ alkyl.

12. The process of claim 1 wherein X is H, Cl, or $CH_3$; Y is H and R is $C_1$–$C_2$ alkyl.

13. The process of claim 1 wherein the catalyst is prepared from zirconium tetrachloride or a zirconium tetraalkoxide.

14. The process of claim 1 wherein the catalyst is prepared in situ from zirconium tetrachloride and the phenol.

15. The process of claim 1 wherein the molar ratio of catalyst to disulfide is 0.05:1–0.2:1.

16. The process of claim 2 wherein the molar ratio of catalyst to disulfide is 0.05:1–0.2:1.

17. The process of claim 7 wherein the molar ratio of catalyst to disulfide is 0.05:1–0.2:1.

18. The process of claim 11 wherein the molar ratio of catalyst to disulfide is 0.05:1–0.2:1.

19. The process of claim 12 wherein the molar ratio of catalyst to disulfide is 0.05:1–0.2:1.

20. The process of claim 13 wherein the molar ratio of catalyst to disulfide is 0.05:1–0.2:1.

21. The process of claim 14 wherein the molar ratio of catalyst to disulfide is 0.05:1–0.2:1.

* * * * *